(12) United States Patent
Buchanan

(10) Patent No.: US 6,955,536 B1
(45) Date of Patent: Oct. 18, 2005

(54) MOTOR CONTROL SYSTEM FOR ENDODONTIC HANDPIECE PROVIDING DYNAMIC TORQUE LIMIT TRACKING OF SPECIFIC FILE FATIGUE

(76) Inventor: L. Stephen Buchanan, 2335 Foothill La., Santa Barbara, CA (US) 93105

(*) Notice: Subject to any disclaimer, the term of this patent is extended or adjusted under 35 U.S.C. 154(b) by 217 days.

(21) Appl. No.: 10/670,102

(22) Filed: Sep. 24, 2003

Related U.S. Application Data

(60) Provisional application No. 60/413,087, filed on Sep. 24, 2002.

(51) Int. Cl.[7] ................................. A61C 5/02
(52) U.S. Cl. .................. 433/27; 435/102; 435/131
(58) Field of Search ................ 433/27, 76, 102, 433/103, 106, 114, 131

(56) References Cited

U.S. PATENT DOCUMENTS

| | | | | |
|---|---|---|---|---|
| 4,243,388 A | * | 1/1981 | Arai | 433/27 |
| 4,723,911 A | * | 2/1988 | Kurtz | 433/27 |
| 4,955,810 A | * | 9/1990 | Levy | 433/72 |
| 5,116,168 A | * | 5/1992 | Aihara | 408/1 R |
| 5,538,423 A | * | 7/1996 | Coss et al. | 433/27 |
| 5,543,695 A | * | 8/1996 | Culp et al. | 318/432 |
| 5,980,248 A | * | 11/1999 | Kusakabe et al. | 433/27 |
| 6,017,354 A | * | 1/2000 | Culp et al. | 606/170 |
| 6,090,123 A | * | 7/2000 | Culp et al. | 606/180 |
| 6,128,966 A | * | 10/2000 | Usui et al. | 73/865.8 |
| 6,293,795 B1 | * | 9/2001 | Johnson | 433/118 |
| 6,329,778 B1 | * | 12/2001 | Culp et al. | 318/434 |
| 6,491,522 B1 | * | 12/2002 | Jensen | 433/215 |
| 6,591,698 B1 | * | 7/2003 | Carlsson et al. | 73/862.18 |
| 6,616,446 B1 | * | 9/2003 | Schmid | 433/27 |
| 6,866,509 B2 | * | 3/2005 | Jensen | 433/215 |

FOREIGN PATENT DOCUMENTS

EP  1 400 217  * 3/2004

* cited by examiner

*Primary Examiner*—Ralph A. Lewis
(74) *Attorney, Agent, or Firm*—Henry M. Bissell

(57) ABSTRACT

A system for establishing a cumulative history of stress factors encountered during use of an endodontic file and keeping track of such for a plurality of files so that the files can be re-used with confidence that a given file is as safe to use as a new file. Cost of file maintenance is significantly reduced and the likelihood of file breakage in use is minimized.

17 Claims, 4 Drawing Sheets

MOTOR CONTROL SYSTEM FOR ENDODONTIC HANDPIECE PROVIDING DYNAMIC TORQUE LIMIT TRACKING OF SPECIFIC FILE FATIGUE

CROSS-REFERENCE TO RELATED APPLICATION

This application claims priority from U.S. Provisional Application Ser. No. 60/413,087, filed Sep. 24, 2002.

BACKGROUND OF THE INVENTION

1. Field of the Invention

The present invention generally relates to a computerized control system for the drive motor of a dental handpiece and, more particularly, to such a control system for taking account of the condition of cutting tools used in the handpiece.

2. Description of the Related Art

Dental handpieces are used in root canal work for motorized driving of root canal files and other cutting implements. The breaking of a root canal file is a serious event, particularly where the broken end of the file may remain embedded in the root canal of the tooth. File breakage, as currently understood, occurs when torsional stress thresholds for a given instrument are exceeded during its rotation in the tooth. Also contributing to this instrument failure is the accumulation of cyclic fatigue as this instrument rotates in root canals that are curved. Such cyclic fatigue develops due to the tensile stretching that occurs in this file on the outside of its curvature and the compression that occurs on the inside curvature at that same location along the file's length. This compression/tension event is magnified by the rapid rotation of the instrument during root canal preparation procedures, alternately stretching and compressing the file around its circumference.

Numerous efforts have been made by innovators in the field to limit file breakage primarily by measuring torque values imparted to the file during root canal shaping procedures and to take corrective steps, such as sounding an audible warning and/or slowing, stopping or reversing the handpiece motor when a reference level is reached. However, this torque limitation safety feature does not take account of accumulated fatigue which may contribute to a reduction of permissible torque limit for a given instrument, or the curvature of the root canal being shaped, thus resulting in actual breakage. Neither does it account for the variations in structural characteristics of the different shaping files used to prepare a root canal.

A number of examples of such efforts from the prior art are set out in the following.

U.S. Pat. No. 4,243,388 of Arai discloses a dental hand engine for driving a reamer for root canals. The disclosed system incorporates a control device which electrically senses when the forward end of the reamer reaches the radical apex of a tooth root canal so that the engine and its reamer may be automatically stopped.

U.S. Pat. No. 4,955,810 of Levy discloses apparatus and method for measuring thickness of the dentin layer of a patient's tooth. In the disclosed process, the resistance to electrical current flow from a voltage applied between the dentin and a spaced apart region of the patient's body is used to indicate the thickness of the dentin layer. U.S. Pat. No. 5,538,423 of Coss et al. discloses a dental drilling system having a programmable control unit for controlling operating parameters of the drilling system, such as direction of rotation, speed of rotation, torque of the dental drill tool bit, pumped irrigation fluid flow rate, and the intensity of light from a light source, to name a few. The control unit may be programmed with sets of data values representing a desired value for each of the operating parameters to be controlled. The system is said to accurately achieve and maintain a specified rotation speed or torque.

U.S. Pat. No. 4,723,911 of Kurtz discloses apparatus for high-speed drilling of bone tissue of varying density to produce proportioned variations in the speed of the drill. Instantaneous bur rotational speed is automatically sensed to produce a signal representing a change in speed, correlating to an indication of the density of the bone tissue.

A number of systems for controlling motor speed or other parameters of a drill system outside the field of endodontics are known. For example, U.S. Pat. No. 5,038,084 of Wing describes a closed loop control system which senses the current of a drill motor in order to cause the drill motor to slow down as current decreases, such as when the drill cuts through a workpiece.

U.S. Pat. No. 5,543,695 of Culp et al. discloses a powered medical instrument including a manually operable foot switch for a motor control unit coupled to an autoclavable handpiece. In operation, a maximum torque value is set for a control circuit which limits the motor torque to the selected value.

U.S. Pat. No. 5,116,168 of Aihara discloses a control system for a machine drill making holes through a composite workpiece made of materials having different machining properties. Sensors detect feed speed and rotational speed, respectively, as well as thrust force applied to the drill. The resulting sensor signals are compared with optimum values to control the feed speed and rotational speed of the drill.

U.S. Pat. No. 4,822,215 of Alexander discloses an automatic drill system which also utilizes thrust and torque sensors for enabling a computer to control the drill for an efficient drilling operation for laminated materials, a non-dental application.

U.S. Pat. No. 5,980,248 of Kusakabe et al. discloses a motor controller for a dental handpiece which uses signals from a torque sensor which detects the load torque applied to the cutting tool to either stop the drive motor, reduce the rotational speed thereof or temporarily reverse motor direction when the detected load torque has reached a preset reference value. This system is said to prevent a cutting tool, such as a relatively slender file for root canal formation, from breaking during the procedure.

The breaking of a root canal file with the broken-off part remaining in the tooth undergoing treatment represents somewhat of a disaster. Any system which relies on the sensing of drive motor torque or file tip position and comparing the read-out signals with preset reference levels is still subject to failure (i.e., file breakage) when the reference levels are not set properly.

Unexpected file breakage in a system in which the torque or other parameter sensors are functioning properly and the preset reference levels are within normal limits can still occur in instances where the file itself may have developed fatigue from repeated use in the standard endodontic procedure so that its likelihood of breakage is no longer governed by the statistical data applicable to a standard population of unused files.

Unexpected file breakage can also be caused by obvious and hidden canal curvatures. Canal curvatures which introduce fatigue to files range from even slight coronal curvatures to severe apical curvatures. Furthermore, molar root canal curvatures are always multiple in number and multiplanar in direction. Endodontic shaping files are subject to cyclic fatigue when curvatures are significant, even when the canal is relatively large and little torsional stress is imparted to its fatigue history. Even the largest file diameters will break when challenged by cyclic fatigue.

Fatigue in any drilling implement is difficult to determine. Therefore it is difficult to predict whether a given drill will perform satisfactorily in a control system where the reference limit values are standard and where the sensors for measuring torque or other parameters are performing properly.

SUMMARY OF THE INVENTION

In brief, arrangements in accordance with the present invention involve a system which measures operating parameters relating to the fatigue factor in a drill so that the drill may be discarded or the rotational speed and/or torque limits be dynamically reduced in proportion to the accumulated fatigue at some point in the repetitive use cycle where the predicted fatigue level in the drill warrants discontinuing any further use at the most basic level. This handpiece system records the total number of revolutions each individual file has turned, as well as the torsional stresses accumulated during those revolutions. It may also keep track of other operating factors which bear on accumulated fatigue such as, for example, the direction of rotation, the speed of rotation, and the torque at the file tip, as well as the size and taper of the file being used. It keeps track of this data on an individual file basis, displaying the data as desired when a file is selected for re-use (after sterilization) and using it to provide an appropriate torque limit for the starting point for the next period of use.

In accordance with one aspect of the invention, provision is made for storing individual files in autoclavable file storage boxes. An operative connection is established between the storage boxes and the control system computer to provide a display of the data history of a given file upon command. In this manner, the professional is able to match a given file to the anticipated usage for a particular task. In simple terms, if a short duration drilling task is encountered, a drill may be selected which already has a significant fatigue data history, and the control system could drive the drill at speeds and torques which are below the predicted limits of breakage for that particular drill. On the other hand, such a drill would be avoided if the task to be performed is likely to involve higher levels of stress which might be more likely to result in breakage during the anticipated task.

Another method of use would be for this device to simply indicate when individual files in a sterilization organizer box should be replaced. In accordance with this aspect, a method is disclosed by which the system microprocessor can keep track of many individual files and many different file sets in the doctor's office. As it is now, whole sets of instruments are discarded after one procedure in an attempt to err on the careful side, by using fresh files at the start of every case. This is much better than the risky process of using the same file in a certain number of canals which requires careful marking on used files and it only counts the number of canals cut; this is not safe enough. While using new files greatly reduces possible error, it also causes inadvertent profligacy. In the interests of safety, many files are prematurely discarded. Conversely, 20-0.10 files last much longer than 20-0.06's for instance. Small new files could still be broken when a second new file should be brought in before the end of that procedure.

Another critical factor, after the design and fatigue history of instruments, is the canal curvatures through which the instruments will be required to work. The procedurally important variations of canal curvature are the location of curvature, the radius of curvature, and finally, the degree of curvature. With that said, each root canal often has multiple curvatures, each of them again has a different location, acuity, and degree of curvature. The fact that many of these curvatures are hidden in clinical radiographs further challenges the clinician in preventing file breakage.

Systems of the invention may also include a testing model which will consistently replicate specific root canal dimensions and curvatures in dentin and synthetic materials so that many of the same size and geometry of specific endodontic instruments can be tested to failure in many identical and anatomically correct root canal test models, thereby allowing greater predictability in the anticipation of future failures of those same files in clinical practice. In accordance with this aspect, a method is disclosed by which the system microprocessor can keep track of many individual files and many different file sets in the doctor's office.

Fatigue in a dental drill develops as a function of the number of occasions and length of time when the stress applied with a given parameter has exceeded the elastic limit for that parameter, thereby incurring a change, however slight and undetectable, in drill quality. This introduces fatigue such that, if operation of the drill is continued, the risk of breakage may be significantly increased. The specific figures for the elastic limits to be taken into account in tracking the accumulated fatigue for a given dental drill may be provided by the manufacturer of the drill. However, manufacturing testing seldom matches clinical conditions. Also what is needed to be recorded is the number of times a given torque limit was hit or approached, also the duration at the limit and the torque value as well as the number of rotations. If not so provided, they may be determined empirically by testing to destruction of sample drills of a type and set in accordance with an aspect of the invention disclosed above. The result will be an increase in the confidence level that a given drill may be used with reduced likelihood of breakage.

Each of the parameters which are understood to contribute to accumulated fatigue during use of a given drill may have a determinable strain limit which can be used in operating a control system to prevent a given drill from reaching its fatigue limit. Operating a drill with such a control system not only significantly reduces the extent of drill breakage in performing root canal work on a tooth, but it serves to prolong drill life, allowing repeated use of a particular drill with safety and confidence that repeated use of the drill is justified.

All of the capabilities of the system to predict file breakage are incumbent upon correctly modeling the fatigue curve for each type and size of instrument as they shape different root canal morphologies. Heretofore there has been no known method that could simulate specific root canal anatomy and accurately replicate the stresses placed on files in that environment. Extracted teeth have traditionally been used to test prototype instruments as well as to teach dentists the use of new instruments and techniques; however, they are limited in their use in determining fatigue curves due to the virtually infinite variability of natural root canals.

Testing and teaching has also been done in the field with epoxy-resin root canal models which can be made with reproducible diameters and curvatures. However, all of the artificial materials used to date behave very differently from the dentin encountered in root canals, specifically by softening in the presence of heat caused by cutting activity as well as by lacking the "lubricity" of dentin, thus severely limiting the accuracy of data recovered.

One particular embodiment of the invention involves a bovine dentin model that answers all of these problems. Because cow molars are much larger than human teeth, several slabs of bovine dentin can be sliced off each cow tooth. These are then each milled flat on one side so that two of them may be clamped together after several simulated root canals are cut into each half. The canal halves are routed out of the bovine dentin blocks with a computer-numerically-controlled milling machine so that canal contours can be accurately reproduced in the block-halves.

With this machine technology, literally any canal morphology a researcher wants to test files in could be cut in the block-halves, either by manual design (dialing in diameters, tapers, and curvatures) or better by using computer models of canals reconstructed from microCT scans of extracted teeth. Most important in research terms is the exact reproducibility of these models, thereby increasing the accuracy of the predictive research and application of the fatigue curve for each of the instruments in all of the classic anatomic challenges presented by root canal systems. In this method the morphologies of different canals are subtracted from the computer reconstruction of the tooth, laid out as curvatures in two dimensions, programmed into the CNC machine, and the canal is cut into the two block-halves exactly as it was in the original tooth. Another method is to cut the canal halves with a CNC laser.

A final embodiment that also solves all current problems with modeling file behavior in canals involves using stereolithography to create anatomically correct models of roots and root canals. In this method the computer model of the reconstructed tooth is input to the system, directing a laser beam to photo-polymerize successive layers of the model. The lubricity of the dentin is replicated by mixing either collagen matrix reconstituted from dentin or synthetic fibers with similar lubricity into the photo-polymerized solution. The advantages of this method over the bovine test model is the ability to reproduce classic dental morphology quickly and relatively cheaply, with virtually perfect anatomic accuracy, while maintaining adequate functional characteristics such as dentin hardness and lubricity.

Whether the model is bovine dentin or resin, by testing each file type and size to failure repeatedly in specific, reproducible canal forms, a very accurate fatigue curve can be drawn for that instrument operating in that type of canal. However, a variable still remaining is a way to accurately assess the amount of curvature in a canal, since so many canals have curvatures hidden in normal views of dental x-rays. Another embodiment of the invention is an instrument to "read" the curves in a patient's root canals. After a root canal has been negotiated and enlarged to a 15-0.02 K-file size, a non-cutting file probe is placed into the handpiece, the curve measurement function is switched on the handpiece control, and the probe is taken to length in the canal. The controller measures the torsional resistance to rotation of the smooth-sided probe in the canal and factors that into the torsional stress history of each file used in that canal so that a more accurate estimate may be made of when the fatigue curve for that file has gone into dangerous territory. The same probes are spun in each of the simulated canal models the files are tested in, so that each of the fatigue curves generated can be related to a specific amount of canal curvature. Then, when the clinician uses the curvature probe to measure the curves of the canal to be shaped, the computer can choose the correct fatigue curve in predicting failure of that file in that canal.

With individual file data collected and correlated with corresponding files through the procedures described above, it may be expected that the use of systems in accordance with the present invention will not only make it possible for the professional to perform his or her task with significantly reduced risk of file breakage under circumstances which may adversely affect the patient, but the cost of the files used by the professional over a given period of time will be significantly reduced.

BRIEF DESCRIPTION OF THE DRAWINGS

A better understanding of the present invention may be realized from a consideration of the following detailed description, taken in conjunction with the accompanying drawings, in which.

DESCRIPTION OF THE PREFERRED EMBODIMENTS

Figure 1:
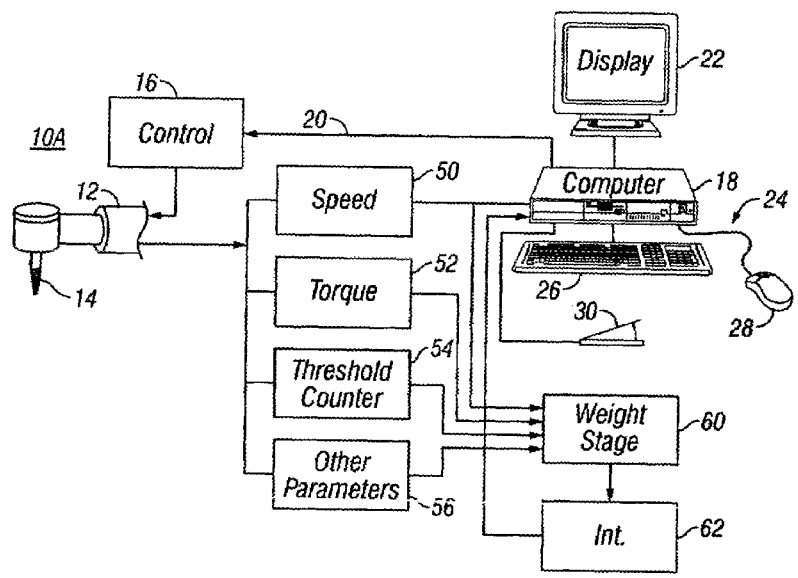
FIG. 1 is a schematic block diagram of a first portion of one particular arrangement in accordance with the invention.
Figure 2:
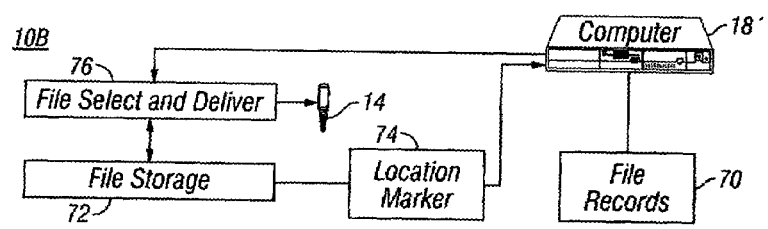
FIG. 2 is a schematic block diagram of a second portion of the system of the invention.

FIGS. 1 and 2 together illustrate a system 10 comprising a data collection portion 10A (FIG. 1) and a file selector portion 10B (FIG. 2).

The data collection portion 10A is shown comprising a handpiece 12 having a file 14 installed therein. The handpiece 12 is controlled in its operation by a control stage 16 which operates in response to signals from a computer 18 over a connecting line 20. Computer 18 is equipped in conventional fashion with a display device 22 and one or more input devices 24 which may be a keyboard 26, a mouse 28, a foot control 30 and/or other similar devices such as a trackball, a touchscreen, a touchpad, and the like.

The data collection portion 10A also includes a number of sensors, such as a speed sensor 50, a torque sensor 52, a threshold counter 54 and one or more sensors 56 to keep track of other parameters relating to the handpiece tool 12. Each of these sensors receives as its input corresponding outputs from the handpiece tool 12. Each sensor 50, 52, 54, 56, converts its input from the handpiece tool 12 into signals which are appropriate for the processing and ultimate collection as data in a computer 18. They may be applied directly to the computer 18 or, if desired, they may be processed in a weighting stage 60 and an integrator 62 before being stored in the computer 18. The file selection portion of FIG. 10B is shown as comprising a computer 18', which may be the computer 18 of FIG. 1, coupled to a file records stage 70 where records corresponding to the individual files are stored for selection in the file selection portion 10B. The file selection portion further includes a file storage member 72, a location marker stage 74 which is connected between the file storage member 72 and the computer 18', and a stage 76 for selecting and delivering a file such as 14 from the file storage member 72. In one embodiment the file storage member 72 is an autoclavable box having a plurality of slots or pockets for receiving individual files for reuse.

In operation of the system 10, a number of endodontic files are provided with unique identification codes. These unique codes are entered into the computer 18, together with data regarding the various file parameters, such as file type, file size, and the like. If the files have been used, the individual file records also contain the data derived by way of the sensors of FIG. 1 from the operation of the file 14 and the handpiece 12. These files are placed in the file storage box 72 with their individual locations noted by the location marker 74 and stored as part of the record in the computer 18'. When the professional needs to select a file for a particular root canal preparation, he enters the desired parameters into the computer and the computer monitor displays the data of, for example, five particular files which are in the storage box 72. The professional may select one of the files presently displayed (using the cursor and the ENTER key) or he may cause the computer to bring up another five files for display on the monitor. As an alternative option, the professional may plug in the file box and simply select from files in the "used" section until they slow down to uselessness and are replaced with the "reset" button being pushed. Once a particular file is selected, it can be retrieved manually or the retrieval mechanism of the select and deliver stage 76 can be used to retrieve the file from the storage box and deliver it to the dental office site.

In the operation of the preferred embodiment, each dental office will have a number of endodontic file boxes, each with identification numbers. Each specific file location in each specific file box is coded. These file boxes are specifically designed for each of the file systems available so that a file storage tube exists, and is labeled for each file geometry in that specific shaping system. When a file is selected for use the sensor adjacent to the now-empty file tube signals as such to the handpiece computer. The computer knows the fatigue curve of that file geometry and manufacturer, the fatigue history of that specific file, and the canal curvatures and locations of said curvature.

Alternatively, each file could have a unique ID number on it, said ID number tracking any of a number of methods, including but not limited to bar codes, magnetic code, subtle shank geometry codes. When the dentist needs another file, he or she keys the box and specific file code into the handpiece control unit, or simply by pulling out the file from the box, the handpiece control computer knows which file is being used.

In this system, when a file is selected for use, the computer looks at accumulated cycles and torque values and sets a dynamic torque limit appropriate for that file geometry and that file's history of use, and the canal curves in the canal to be shaped. At a threshold point the file is discarded because the handpiece controller display says so or because the dynamic torque limit is too low to cut effectively.

Figure 3:
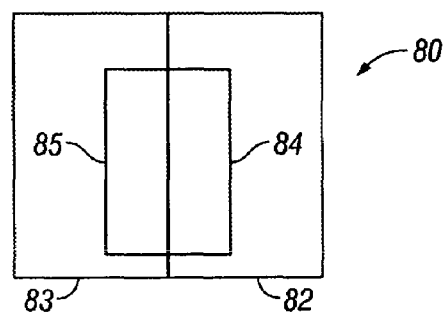
FIG. 3 is a schematic drawing of a two-part block encasing a simulated root canal.
Figure 4:
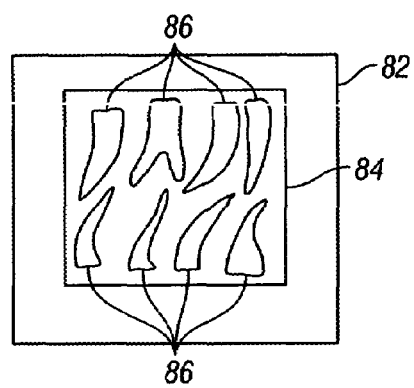
FIG. 4 is a schematic drawing of one of the parts of the block shown in FIG. 3.

FIGS. 3 and 4 illustrate a block containing sections of a cow's tooth prepared for use with the system of the invention. In FIG. 3, a block 80 is shown comprising two half-blocks 82, 83. Slabs 84, 85 represent sections taken from a cow's tooth.

In FIG. 4, the half-block 82 is shown containing the slab 84 of a sectioned cow's tooth. In the slab 84, a plurality of root canals 86 have been cut in accordance with the methods described herein.

Figure 5:
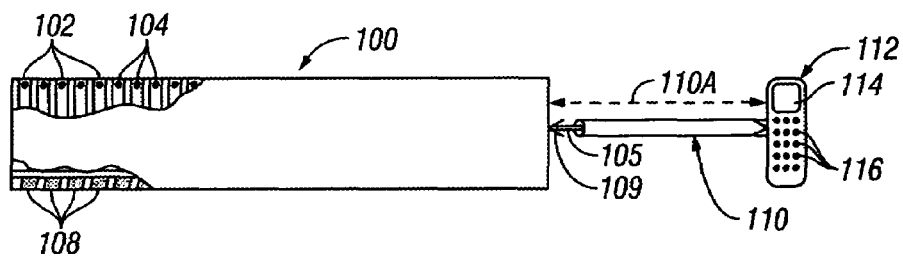
FIG. 5 is a schematic block diagram of a file organization box with sensors at each file location and a communications link that plugs into a handpiece control unit.

FIG. 5 is a schematic block diagram of a file box and hand control unit comprising a second embodiment in accordance with the invention. FIG. 5 depicts a file storage box 100 partially broken away to show a plurality of file storage compartments 102, each provided with a sensor 104 and a file ejector 108. The sensors 104 are individually connected to a cable 105 in a link 110 to feed file identification signals to a hand held control member 112. In conventional fashion, similar to a cell phone, the control member 112 is provided with a display 114 and control buttons 116, including RESET and ENTER buttons; up, down and side movement arrows; and any other appropriate mode control selectors. The ejectors 108 are individually connected to a cable 109 also contained with the cable 105 in the connecting link 110 to the hand held device. Instead of the wired link 110, the link to the hand held device 112 may be an optical link 110A, or a wireless link.

In the operation of the embodiment of FIG. 5, each file (not shown) is coded with an identification code. This code may contain all of the relevant data for that specific file. When the dentist needs another file, he may simply pull a file out of the box or he may key into the hand-held control box 112 the data representing the parameters of the type of file he is looking for, using the buttons 116 in matching data from acceptable files which are sensed by the sensors 102 as the data appear on the display 114. Selection may then be made by the appropriate buttons 116 and an appropriate ejector 108 may be energized by pressing a return button on the control member 112. The file is then made available for selection or for insertion into the dental handpiece.

Figure 6:
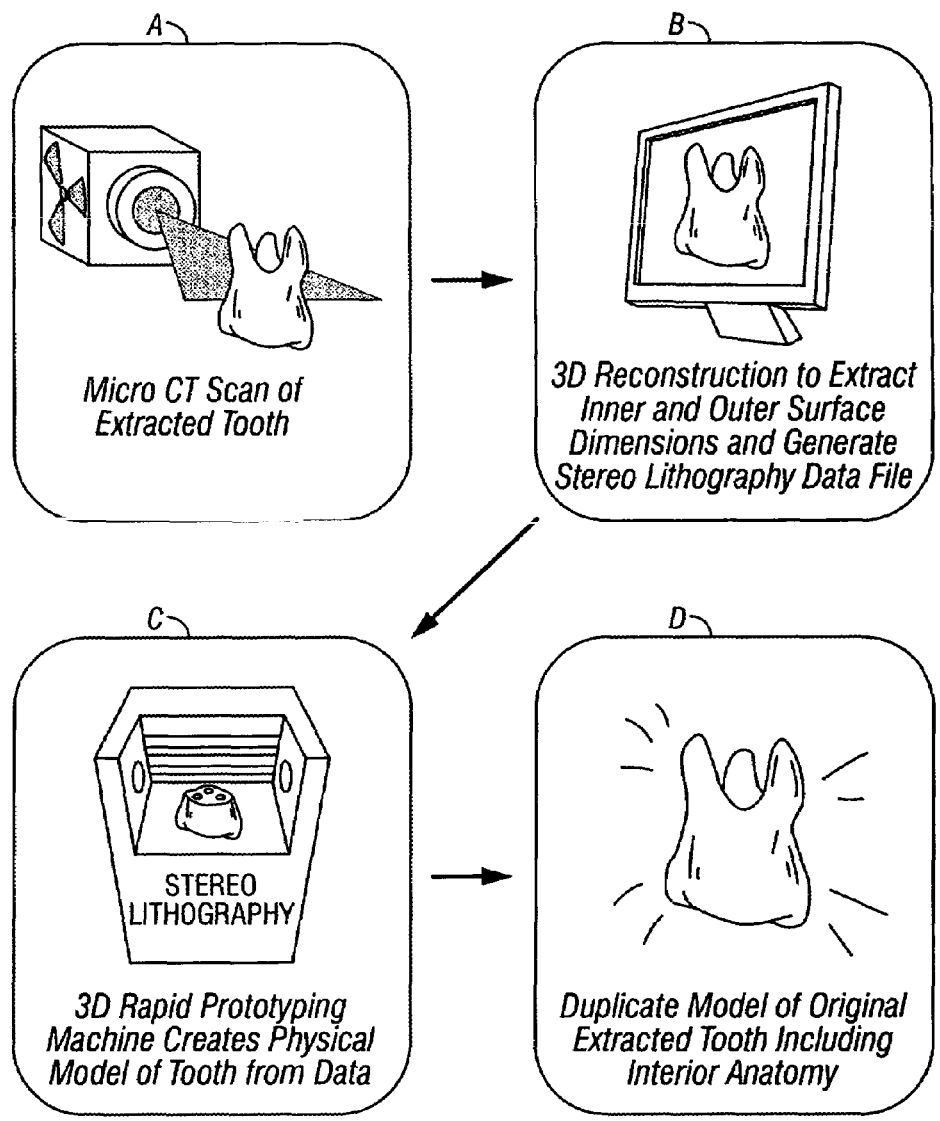
FIG. 6 is a schematic block diagram illustrating a stereo lithographic process applicable to systems of the invention.

FIG. 6 represents, in block diagram form, a process of stereolithography which may be useful in the practice of the present invention. Block A of FIG. 6 represents the first step in the process, which involves a Micro CT scan of an extracted tooth. Block B represents a 3-dimensional reconstruction to extract inner and outer surface dimensions and generate a stereolithography data record. This is followed by Block C representing the step of a 3-dimensional rapid prototyping machine creating a physical model of a tooth from the established data. The result is shown in Block D as a duplicate model of the original extracted tooth, including the interior anatomy.

Figure 7:
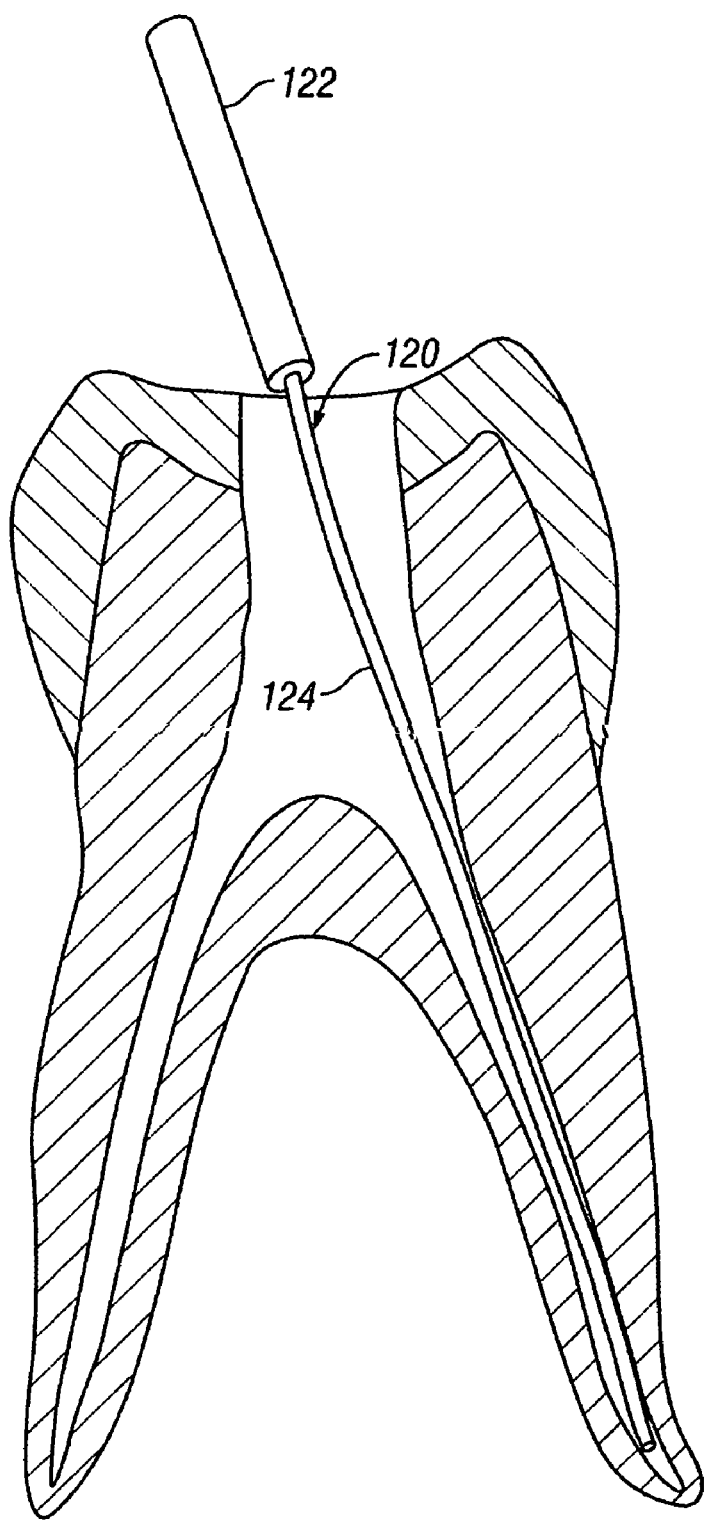
FIG. 7 shows a smooth root canal probe which is used prior to shaping the canal to measure obvious and hidden root canal curvatures.

FIG. 7 is a schematic representation of a tooth in cross-section, with a probe device 120 comprising a handle 122 and a long, thin probe member 124. The member 124 is inserted into the root to the distal end, and is used by the professional to determine the extent of the root canal.

In the practice of embodiments of the invention, it becomes possible to reuse particular files with confidence that the file is safe to use. The computer keeps track of the prior uses of the file, specifically the number of revolutions and the accumulated torsional stresses encountered by the file in previous use, and records this as a cumulative stress history of the file. With this cumulative history, the likelihood of file breakage under specific conditions can be predicted and avoided.

Although there have been described hereinabove various specific arrangements of a MOTOR CONTROL SYSTEM FOR ENDODONTIC HANDPIECE PROVIDING DYNAMIC TORQUE LIMIT TRACKING OF SPECIFIC FILE FATIGUE in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A motor control system for an endodontic handpiece comprising:

means for measuring selected operating parameters related to the fatigue factor in a dental file used in a handpiece during preparation of a root canal;

recording the resulting measurements over time in a computer as the data history of the file;

a file storage box for storing a plurality of individual files, the location of said files in said storage box being correlated in said computer with said individual file data histories;

means for displaying the data history of a given file; and means for permitting selection of a given file according to its displayed data history.

2. The motor control system of claim 1 wherein the measuring means is capable of recording the total number of revolutions a given individual file has turned since its first use.

3. The motor control system of claim 1 wherein the measuring means includes means for measuring the torsional stresses incurred in an individual file during the rotation thereof and means for developing a record thereof.

4. The motor control system of claim 1 wherein the measuring means includes means for tracking direction of rotation of the dental file for the period of use of the file in a given procedure.

5. The motor control system of claim 1 wherein the measuring means includes means for measuring the speed of rotation of said dental file on an incremental basis during the period of use in a given procedure.

6. The motor control system of claim 1 wherein the file selection permitting means includes means for ejecting a selected file from the file storage box where it is stored.

7. The motor control system of claim 6 wherein the means for permitting selection of a given file includes means for identifying a group of stored files having file data histories which correspond closely to specified parameters to permit selection of a given file from said group.

8. The motor control system of claim 1 wherein said file storage box is autoclavable so that the files stored therein may be sterilized for subsequent use.

9. The method of controlling a drive motor for an endodontic handpiece comprising the steps of:

measuring selected operating parameters related to the fatigue factor in a dental file used in a handpiece during preparation of a root canal;

recording the resulting measurements over time in a computer as the data history of the file;

storing individuals files in a file storage box wherein the location of said files is correlated in said computer with said individual file data histories;

displaying the data histories of the given files; and permitting a given file to be selected in accordance with the displayed file data history.

10. The method of claim 9 wherein the recording step includes the step of recording the total number of revolutions a given individual file has turned since its first use.

11. The method of claim 9 wherein the measuring step includes measuring the torsional stresses incurred in an individual file during rotation thereof.

12. The method of claim 11 wherein the measuring step further includes the step of developing a record of accumulated stress.

13. The method of claim 9 wherein the measuring step includes the step of tracking the direction of rotation of a dental file for the period of use of the file in a given procedure.

14. The method of claim 9 wherein the measuring step further includes the step of measuring speed of rotation of said dental file on an incremental basis during the period of use in a given procedure.

15. The method of claim 9 wherein the step of selecting a given file further includes the step of ejecting the selected file from its stored position in the file storage box.

16. The method of claim 15 wherein the selecting step comprises the step of identifying a group of stored files having file data histories which correspond closely to specified parameters to permit selection of a chosen file from said group.

17. The method of claim 9 further comprising the step of storing said files in an autoclavable storage box.

* * * * *